United States Patent
Karlsson

(10) Patent No.: US 11,021,580 B2
(45) Date of Patent: Jun. 1, 2021

(54) PROCESS FOR EFFICIENT CROSS-LINKING OF HYALURONIC ACID

(71) Applicant: Galderma Holding SA, La Tour-de-Peliz (CH)

(72) Inventor: Morgan Karlsson, Knivsta (SE)

(73) Assignee: Galderma Holding SA, La Tour-de-Peilz (CH)

( * ) Notice: Subject to any disclaimer, the term of this patent is extended or adjusted under 35 U.S.C. 154(b) by 0 days.

(21) Appl. No.: 15/747,648

(22) PCT Filed: Jul. 18, 2016

(86) PCT No.: PCT/EP2016/067072
§ 371 (c)(1),
(2) Date: Jan. 25, 2018

(87) PCT Pub. No.: WO2017/016917
PCT Pub. Date: Feb. 2, 2017

(65) Prior Publication Data
US 2018/0223053 A1    Aug. 9, 2018

Related U.S. Application Data

(63) Continuation of application No. PCT/EP2016/067072, filed on Jul. 18, 2016.

(30) Foreign Application Priority Data

Jul. 27, 2015 (EP) ..................................... 15178526

(51) Int. Cl.
| | | |
|---|---|---|
| *C08J 3/24* | (2006.01) | |
| *C08B 37/08* | (2006.01) | |
| *C08L 5/08* | (2006.01) | |
| *A61K 8/73* | (2006.01) | |
| *A61K 31/728* | (2006.01) | |
| *A61K 47/36* | (2006.01) | |
| *A61K 9/06* | (2006.01) | |
| *A61Q 19/08* | (2006.01) | |
| *A61L 27/20* | (2006.01) | |
| *C08J 3/075* | (2006.01) | |

(52) U.S. Cl.
CPC ................. *C08J 3/24* (2013.01); *A61K 8/735* (2013.01); *A61K 9/06* (2013.01); *A61K 31/728* (2013.01); *A61K 47/36* (2013.01); *A61L 27/20* (2013.01); *A61Q 19/08* (2013.01); *C08B 37/0072* (2013.01); *C08J 3/075* (2013.01); *C08L 5/08* (2013.01); *A61K 2800/91* (2013.01); *A61L 2430/34* (2013.01); *C08J 2305/08* (2013.01); *C08L 2201/54* (2013.01); *C08L 2203/02* (2013.01)

(58) Field of Classification Search
None
See application file for complete search history.

(56) References Cited

U.S. PATENT DOCUMENTS

| | | |
|---|---|---|
| 4,716,154 A | 12/1987 | Mälson et al. |
| 6,685,963 B1 | 2/2004 | Taupin et al. |
| 6,921,819 B2 | 7/2005 | Piron et al. |
| 7,741,476 B2 | 6/2010 | Lebreton |
| 8,357,795 B2 | 1/2013 | Lebreton |
| 8,574,629 B2 * | 11/2013 | Gavard Molliard .... A61L 27/20 424/486 |
| 2005/0281880 A1 | 12/2005 | Wang |
| 2006/0105022 A1 | 5/2006 | Yokokawa et al. |
| 2007/0066816 A1 | 3/2007 | Tsai et al. |
| 2009/0155362 A1 | 6/2009 | Longin et al. |
| 2010/0261893 A1 * | 10/2010 | Chen ................... C08B 37/0072 536/123.1 |
| 2010/0266512 A1 | 10/2010 | Wenk et al. |
| 2010/0316683 A1 | 12/2010 | Piron et al. |
| 2011/0262489 A1 * | 10/2011 | Zhao .................... A61K 9/0021 424/400 |
| 2012/0172328 A1 * | 7/2012 | Lebreton .................. A61K 8/42 514/54 |
| 2013/0172288 A1 | 7/2013 | Bon Betemps et al. |

FOREIGN PATENT DOCUMENTS

| | | | |
|---|---|---|---|
| CN | 102727424 A * | 10/2012 | ............... A61K 9/06 |
| EP | 2 236 523 A1 | 10/2010 | |
| FR | 2 918 377 A1 | 1/2009 | |
| WO | WO 02/05753 A1 | 1/2002 | |

(Continued)

OTHER PUBLICATIONS

He et al., CN 102727424 A,2012, machine translation, Retreived on Jan. 29, 2019 from http://worldwide.espacenet.com (Year: 2012).*
International Search Report (PCT/ISA/210) dated Oct. 12, 2016, by the European Patent Office as the International Searching Authority for International Application No. PCT/EP2016/067072.
Written Opinion (PCT/ISA/237) dated Oct. 12, 2016, by the European Patent Office as the International Searching Authority for International Application No. PCT/EP2016/067072.

*Primary Examiner* — Dale R Miller

(74) *Attorney, Agent, or Firm* — Foley & Lardner LLP; Sunit Talapatra

(57) ABSTRACT

A process for manufacturing a cross-linked hyaluronic acid (HA) gel product is comprising the steps of: (a) preparing an aqueous mixture of HA and a cross-linking agent selected from multiepoxides and diepoxides; wherein the HA is dissolved in an aqueous solution containing 1-10% (w/w) inorganic hydroxide; and wherein the dissolved HA constitutes more than 10% (w/w) of the final mixture; and (b) subjecting the aqueous mixture to cross-linking conditions to allow the dissolved HA to react with the cross-linking agent so as to obtain a cross-linked HA gel product.

13 Claims, 2 Drawing Sheets

(56) References Cited

FOREIGN PATENT DOCUMENTS

| WO | WO 2010/029344 A1 | 3/2010 |
| WO | WO 2013/164782 A1 | 11/2013 |
| WO | WO 2014/206500 A1 | 12/2014 |
| WO | WO 2014/206701 A1 | 12/2014 |

\* cited by examiner

PROCESS FOR EFFICIENT CROSS-LINKING OF HYALURONIC ACID

FIELD OF THE INVENTION

The present invention relates to the field of polysaccharides. More specifically, the present invention is concerned with novel processes of cross-linking hyaluronic acid (HA) and of manufacturing cross-linked HA products.

BACKGROUND OF THE INVENTION

One of the most widely used biocompatible polymers for medical use is hyaluronic acid (HA). It is a naturally occurring polysaccharide belonging to the group of glycosaminoglycans (GAGs). HA and the other GAGs are negatively charged heteropolysaccharide chains which have a capacity to absorb large amounts of water. HA and products derived from HA are widely used in the biomedical and cosmetic fields, for instance during viscosurgery and as a dermal filler.

Water-absorbing gels, or hydrogels, are widely used in the biomedical field. They are generally prepared by chemical cross-linking of polymers to infinite networks. While native HA and certain cross-linked HA products absorb water until they are completely dissolved, cross-linked HA gels typically absorb a certain amount of water until they are saturated, i.e. they have a finite liquid retention capacity, or swelling degree.

Since HA is present with identical chemical structure except for its molecular mass in most living organisms, it gives a minimum of reactions and allows for advanced medical uses. Cross-linking and/or other modifications of the HA molecule is necessary to improve its resistance to degradation or duration in vivo. Furthermore, such modifications affect the liquid retention capacity of the HA molecule. As a consequence thereof, HA has been the subject of many modification attempts.

When preparing gels from biocompatible polymers, it is advantageous to ensure a low degree of cross-linking so as to maintain a high bio-compatibility. However, often a more dense gel is required to have a proper biomedical effect, and in such a case the biocompatibility will often be lost.

In the prior art, it has generally been assumed that all or most of the added cross-linking agent is actually incorporated in the cross-linked product.

EP 2 236 523 A1 discloses reacting HA with a cross-linking agent at 10-30° C. for a reaction time greater than 48 h under basic conditions to obtain a cross-linked hyaluronic acid with a low amount of reactive cross-linking agent incorporated in the cross-linked product.

WO 2010/029344 A2 discloses a process for preparing a HA cryogel, wherein a mixture of HA, NaOH and a cross-linking agent is cooled rapidly to avoid cross-linking reactions occurring in solution.

US 2007/066816 A1 discloses a method for producing a double cross-linked HA material under modest basic conditions and/or low HA concentrations.

WO 2014/206701 A1 discloses a process for preparing a cross-linked HA product, wherein a cross-linking reaction occurs in a precipitated state.

There is a need for a process of manufacturing cross-linked HA products having suitable liquid retention capacity and degradation profile, but with retained biocompatibility. In particular, it is desirable to minimize the degree of modification that is needed to obtain a HA gel product having a desired gel strength. It is also desirable to improve the efficiency of the cross-linking reaction and the utilization of the added cross-linking agent.

SUMMARY OF THE INVENTION

It is a purpose of the present invention to provide a novel process for manufacturing a cross-linked hyaluronic acid (HA) gel product, which meets one or more of the following requirements:
Efficient incorporation of cross-linking agent
Limited side reactions, e.g. with surrounding medium and halide ions
Sufficient gel strength to resist deformation and migration when implanted.

The present invention provides versatile control of the HA cross-linking process by controlling the modification efficiency for a particular cross-linking agent with HA, i.e. controlling the efficiency of the cross-linking procedure in producing a gel of desired strength. The present invention therefore allows for manufacturing of a gel having a desired strength (a limited swelling degree) with a surprisingly low chemical modification of the HA. This is advantageous in order to minimize problems with biocompatibility, but generally also to improve control of the HA cross-linking process and to achieve efficient incorporation of the cross-linking agent.

It is also an object of the present invention to provide a process for manufacturing a cross-linked HA gel product wherein a high proportion of the bound cross-linking agent(s) is connected in (at least) two ends, i.e. to achieve a high cross-linking efficiency.

It is a further object of the present invention to provide a process with improved efficiency of the cross-linking reaction.

It is a further object of the present invention to provide a process with improved utilization of the added cross-linking agent.

It is also an object of the present invention to minimize the degree of modification that is needed to obtain a HA gel product having a desired gel strength.

It is a further object of the present invention to obtain a HA gel product having a long in vivo duration and at the same time a limited degree of modification.

It is also an object of the invention to obtain a HA gel product with useful implantation properties, including gel strength and/or purity from side products and residuals.

For these and other objects that will be evident from this disclosure, the present invention provides according to a first aspect a process for manufacturing a cross-linked HA gel product, comprising the steps of:
(a) preparing an aqueous mixture of HA and a cross-linking agent selected from multiepoxides and diepoxides; wherein the HA is dissolved in an aqueous solution containing 1.5-8% (w/w) inorganic hydroxide; and wherein the dissolved HA constitutes more than 10% (w/w) of the final mixture; and
(b) subjecting the aqueous mixture to cross-linking conditions to allow the dissolved HA to react with the cross-linking agent so as to obtain a cross-linked HA gel product in a single cross-linking step.

It has been realized and demonstrated herein that when using epoxide chemistry for cross-linking HA which is dissolved in water at unusually high concentrations, it is unexpectedly advantageous to conduct the cross-linking process in a narrow pH window. This is achieved by a high, but tightly controlled, presence of hydroxide ions in the concentrated HA solution.

According to another aspect, the present invention provides a product obtainable by the process according to the invention. The product is useful in cosmetic surgery, such as dermal filling, body contouring and facial contouring; and in medical surgery, e.g. dermal filling, body contouring, prevention of tissue adhesion, formation of channels, incontinence treatment, and orthopaedic applications.

Preferred embodiments of these and other aspects of the present invention are evident from the appended claims and the following disclosure, including the examples.

DETAILED DESCRIPTION OF THE INVENTION

Figure 1:
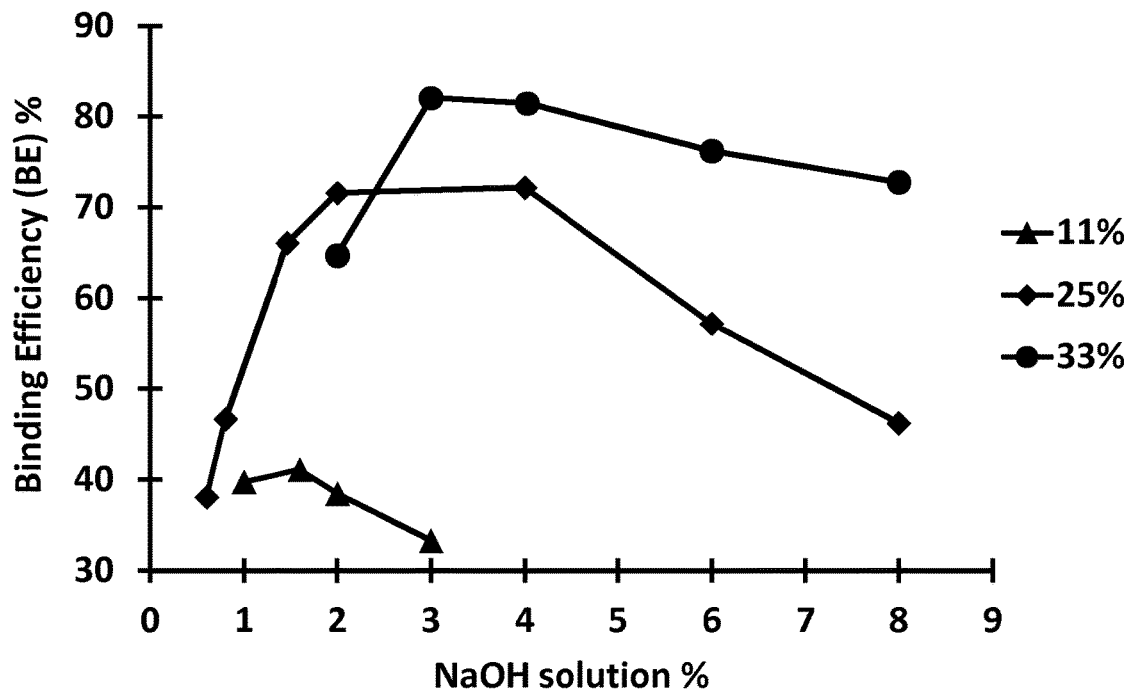
FIG. 1 shows a graph of the binding efficiency for added cross-linking agent as a function of hydroxide concentration for certain HA concentrations.

The present invention is invention is concerned with novel processes of cross-linking HA and of manufacturing cross-linked HA products. It has been realized and demonstrated herein that when using epoxide chemistry for cross-linking HA which is dissolved in water at unusually high concentrations, it is unexpectedly advantageous to conduct the cross-linking process in a narrow pH window. This is achieved by a high, but tightly controlled, presence of hydroxide ions in the concentrated HA solution. As a result, a HA gel product having a desired gel strength with a low degree of modification is provided in a single cross-linking step.

In the prior art, it has generally been assumed that all or most of the added cross-linking agent is actually incorporated in the cross-linked product. It has now been realized that this is far from true, and that the incorporation of the cross-linking agent is typically rather low under traditional cross-linking conditions. In contrast, it has been demonstrated herein that using a high HA concentration in a narrow, high hydroxide concentration range surprisingly provides efficient incorporation of the cross-linking agent.

Unless otherwise provided, the terms "hyaluronic acid" and "HA" are used interchangeably and encompass all variants and combinations of variants of hyaluronic acid, or hyaluronan, of various chain lengths and charge states, as well as with various chemical modifications That is, the term also encompasses the various hyaluronate salts of HA, such as sodium hyaluronate (NaHA). Various modifications of the HA are also encompassed by the term, such as oxidation, e.g. oxidation of $CH_2OH$ groups to $COOH$; periodate oxidation of vicinal hydroxyl groups, optionally followed by reduction or imine formation etc; reduction, e.g. reduction of $COOH$ to $CH_2OH$; sulphation; deamidation, optionally followed by deamination or amide formation with new acids; esterification; substitutions with various compounds, e.g. using a cross-linking agent or a carbodiimide; including coupling of different molecules, such as proteins, peptides and active drug components, to HA; and deacetylation. It is well known to the skilled person that the various forms of HA have different chemical properties that have to be taken into account during chemical modification and analysis. For instance, if it is desired to obtain a solution of HA having a certain pH, the acidity of the material to be dissolved, the acidity of the dissolving liquid and any buffering capacity will all affect the resulting pH of the solution.

It is preferred that the HA substrate is a HA or hyaluronate salt without chemical modifications.

The HA can be obtained from various sources of animal and non-animal origin. Sources of non-animal origin include yeast and preferably bacteria. The molecular weight of a single HA molecule is typically in the range of 0.8-3 MDa, but other ranges of molecular weights are possible, e.g. 0.1-10 MDa.

The product that is manufactured by the method is a cross-linked HA. The method provides ether cross-links between the HA chains, which creates a continuous shaped network of HA molecules which is held together by the covalent cross-links, physical entangling of the HA chains and various interactions, such as hydrogen bonding, van der Waals forces and electrostatic interactions. The cross-linked HA product according to the invention is a gel, or a hydrogel. That is, it can be regarded as a water-insoluble, but substantially dilute, cross-linked system of HA molecules when subjected to a liquid, typically an aqueous liquid.

The resulting cross-linked HA product is preferably biocompatible. This implies that no, or only very mild, immune response occurs in the treated individual.

Since cross-linked HA gel products are highly complex chemical structures, they are typically characterized by a combination of their chemical structures and their physical properties. The deviation in chemical structure from unmodified HA is typically reported as degree of modification, modification degree, cross-linking degree, cross-linking index or chemical modification, which all relate to the amount of cross-linking agent covalently bound to the HA. Throughout this text, the term degree of modification will be used.

The most relevant physical properties of the cross-linked HA gel product are the volume of liquid that the gel can absorb and the rheological properties of the gel. Both properties describe the structural stability of the gel, often referred to as gel strength or firmness, but while the absorption of liquid can be determined for a dry gel, the rheological properties have to be measured on a gel that is swollen to a desired concentration. The measurement yields the resistance of the gel to deformation in terms of elastic modulus (G') and viscous modulus (G"). A high gel strength will give a large resistance to deformation of the gel product swollen to a desired concentration.

According to a first aspect, the present invention provides a process for manufacturing a cross-linked HA gel product. The process is comprising at least (a) a step of preparing an aqueous mixture of the reactants; and (b) a subsequent step of allowing the reactants to cross-link and form a cross-linked HA gel product in a single reaction.

In the initial step (a) of preparing an aqueous mixture of the reactants, an aqueous mixture of HA and a cross-linking agent is prepared. According to the present invention, the HA should be present in higher concentrations than what is commonly used. The dissolved HA constitutes more than 10% (w/w) of the final mixture. The dissolved HA preferably constitutes 15% or more, such as 20% or more, or 25% or more (w/w) of the final mixture. The dissolved HA preferably constitutes 50% or less, such as 45% or less, such as 40% or less, or even 35% or less (w/w) of the final mixture. Preferred ranges of dissolved HA are e.g. 10-50%, such as 15-45%, such as 20-40%, such as 25-35% (w/w) of the final mixture.

The HA is dissolved in the aqueous solution. By the terms "dissolved" and "solution" is understood that the HA is present in a homogeneous mixture with a liquid, in which mixture energetically favourable interactions occur. Addition of liquid to the solution lowers the concentration of the dissolved HA substrate. The solution is aqueous, i.e. it contains water to a major extent except for the HA and the cross-linking agent. The aqueous solution may simply comprise, or even consist, of the HA substrate dissolved in water containing inorganic ions and the cross-linking agent.

Further in the initial step (a) of preparing an aqueous mixture of the reactants, the mixture is prepared by dissolving the HA in an aqueous solution containing a relatively high concentration of hydroxide, preferably 1-10% (w/w). This is typically achieved by dissolving inorganic hydroxide, such as hydroxides of alkali metals, e.g. NaOH, KOH and LiOH; and hydroxides of alkaline earth metals, e.g. $Mg(OH)_2$ and $Ca(OH)_2$, in water prior to adding the cross-linking agent and the HA. It is not critical which inorganic hydroxide is used, and hydroxides of alkali metals, e.g. NaOH, KOH, are preferred e.g. for reasons of economy. A preferred inorganic hydroxide is NaOH. The resulting aqueous solution is preferably comprising more than 1%, such as 1.5% or more, such as 2% or more, such as more than 2.00%, such as 2.1% or more, such as 2.5% or more (w/w) inorganic hydroxide. Importantly, the resulting aqueous solution is at the same time comprising 10% or less, such as 8% or less, such as 6% or less, such as 5% or less, such as 4% or less (w/w) inorganic hydroxide. Preferred ranges of inorganic hydroxide in the solution are e.g. 1.5-8%, such as 1.5-6% (w/w); such as 2-4% (w/w) inorganic hydroxide, especially more than 2.00%, such as 2.1% or more (w/w) inorganic hydroxide which provides strong and firm HA gel products.

The hydroxide concentration in the mixture can also be considered as corresponding to the hydroxide concentration resulting from the above-mentioned concentrations of NaOH, i.e. an hydroxide concentration corresponding to more than 1%, such as 1.5% or more, such as 2% or more, such as more than 2.00%, such as 2.1% or more, such as 2.5% or more (w/w) NaOH, and at the same time corresponding to 10% or less, such as 8% or less, such as 6% or less, such as 5% or less, such as 4% or less (w/w) NaOH. Preferred ranges of hydroxide concentration in the solution are corresponding to e.g. 1.5-8%, such as 1.5-6% (w/w); such as 2-4% (w/w) NaOH, especially. more than 2.00%, such as 2.1% or more NaOH.

It is particularly preferred to combine a high concentration of HA and gradually higher concentrations of inorganic hydroxide within the interval presented as surprisingly useful. It has been experimentally observed that stronger gels can be obtained using more than 2.00%, such as 2.1% or more, such as 2.5% or more or even 4% or more (w/w) inorganic hydroxide in combination with a dissolved HA concentration of 20% or more, or 25% or more (w/w) of the final mixture.

The cross-linking agent employed in the present invention is selected from multiepoxides and diepoxides, preferably diepoxides. Preferred diepoxide cross-linking agents according to the invention include 1,4-butanediol diglycidyl ether (BDDE), 1,2-ethanediol diglycidyl ether (EDDE) and diepoxyoctane, preferably BDDE. Under the strongly basic conditions employed in the cross-linking-step, these cross-linking agents provide ether cross-links between the HA chains. It is not critical which amount of cross-linking agent is used, as long as the cross-linking agent is not completely consumed in the subsequent cross-linking reaction.

The cross-linking agent can be added to the aqueous solution prior to, at the same time as, or after addition of the HA. The cross-linking agent and/or the HA can also be to the aqueous solution added in portions in any suitable order.

In the subsequent step (b) of allowing the reactants to cross-link and form a cross-linked HA gel product, the aqueous mixture prepared in step (a) is subjected to cross-linking conditions, which typically involves a desirable time and temperature. In general terms, this cross-linking step can be made using any high concentration of HA and suitable concentration of cross-linking agent as set out hereinabove, and the time and temperature can vary. The dissolved HA is allowed to react with the cross-linking agent for a suitable time to obtain a cross-linked HA gel product. For avoidance of doubt, this implies that the subsequent step (b) is the only, i.e. single cross-linking step.

The cross-linking step is typically carried out at a temperature of 10-75° C., e.g. 10-40° C., such as 10-35° C. or 10-30° C. but it is preferred that the step is carried out at 15-35° C., such as 15-30° C., and especially at room temperature, e.g. 20-25° C. Preferred temperature ranges are 10-50° C., such as 18-40° C.

The reaction time is suitably in the range of 2-40 h, such as 4-36 h. A longer reaction time than 2 h is useful for reproducibility, especially at larger scale. Longer reaction time than 40 h yields a gel with lower gel strength or may even disrupt the gel entirely. The reaction time is preferably in the range of 8-30 h, such as 12-24 h, e.g. 16-24 h.

In a preferred embodiment, the cross-linking step is performed at 15-35° C. for 2-40 h, such as at room temperature for 16-24 h, to obtain a cross-linked HA gel with excellent implantation properties, in particular gel strength.

Due to the cross-linking, the resulting HA product is a continuous network of interconnected and entangled HA chains which absorbs liquid (swells) and forms a gel. That is, it can be regarded as a water-insoluble, but substantially dilute cross-linked system of HA molecules when subjected to a liquid, typically an aqueous liquid. The gel is mostly liquid by weight and can e.g. contain 90-99.9% water, but it behaves like a solid due to a three-dimensional cross-linked HA network within the liquid. Due to its significant liquid content, the shaped gel is structurally flexible and similar to natural tissue, which makes it very useful as a scaffold in tissue engineering and for tissue augmentation.

The swelling of the resulting HA gel can be allowed to proceed until the gel is fully swollen and no further liquid can be absorbed, or it can be interrupted at an earlier stage to obtain a partially swollen gel. A partially swollen gel can be useful as an intermediate for further processing of the gel, for instance further mechanical production of gel structures of a desired size and shape can be performed. It may also be convenient to use a partially swollen shaped gel product during implantation thereof at a desired site to facilitate administration and minimize patient discomfort and to enhance the lifting capacity by use of the remaining swelling capacity.

If desired, other substances, such as local anaesthetics (e.g. lidocaine hydrochloride), anti-inflammatory drugs, antibiotics and other suitable supportive medications, e.g. bone growth factors or cells, may be added after the cross-linked HA product has been obtained.

The process according to the invention may also comprise one or more further steps.

Optionally, the manufacturing process involves a step of isolating the cross-linked HA product, e.g. by filtration, dialysis or precipitation in a precipitating medium to remove cross-linking agent which has not been incorporated into the HA gel product.

It is particularly preferred to include a step of precipitating the HA gel product after the cross-linking step has been terminated to wash away residual (soluble) cross-linking agent which has not been incorporated into the product. The precipitated HA gel product is then dissolved in any suitable aqueous buffer. Using a higher cross-linker concentration is useful to provide a strong gel, and the increased residual amount of (soluble) cross-linking agent is readily removed with a precipitation step. As a result, a firm and pure HA gel is obtained with excellent implantation properties.

Without being limited thereto, useful precipitation media include pentane, hexane, cyclohexane, 1,4-dioxane, N,N-dimethylformamide, N,N-dimethylacetamide, ethyl acetate, acetamide, diethyl ether, tetrahydrofurane, acetonitrile, methyl ethyl ketone, acetone, lower alkyl alcohols, e.g. methanol, ethanol, propanol, isopropanol and butanol. A preferred group of precipitation media is the lower alkyl alcohols. The term lower alkyl alcohol includes primary, secondary and tertiary alkyl alcohols having from one to six carbon atoms, i.e. $C_{1-6}$ alkyl alcohols. Specific examples of lower alkyl alcohols include methanol, ethanol, denatured spirit, n-propanol, isopropanol, n-butanol, isobutanol, and t-butanol. Preferred lower alkyl alcohols are methanol and ethanol, in particular ethanol, due to price, availability and easy handling.

Optionally, the manufacturing process involves a further step of sterilizing the cross-linked HA product, e.g. by autoclaving, radiation, heating etc., so as to obtain a sterile cross-linked HA product.

According to a related aspect, the present invention provides a cross-linked HA gel product obtainable, or even obtained, by the process according to the invention. The product can advantageously be further characterized by one or more of the following features.

The amount of attached cross-linking agent(s) can be quantified by and reported as the degree of modification (MoD), i.e. the molar amount of bound cross-linking agent (s) relative to the total number of repeating HA disaccharide units. It is preferred that the cross-linked hyaluronic acid product according to the invention has a degree of modification of 1-90 cross-linking agent units per 1000 disaccharide units (0.1-9%), preferably 1-40 cross-linking agent units per 1000 disaccharide units (0.1-4%).

Furthermore, it is preferable that the cross-linked HA gel products according to the invention are viscoelastic. This implies that the gel products exhibit a combination of viscous and elastic properties. As is well known by the skilled person, the viscoelastic properties can be determined with a rheometer. In oscillating mode, the elastic modulus (G') and the viscous modulus (G") can be determined at a frequency of e.g. 0.1 or 1 Hz. For certain viscoelastic gel products according to the invention, it is preferred that the following relationship is satisfied:

$$0.1 \leq \frac{G'}{(G'' + G')} \leq 0.98, \text{ preferably } 0.5 \leq \frac{G'}{(G'' + G')} \leq 0.98.$$

In a preferred embodiment, the elastic modulus G' of the cross-linked HA gel product, when the HA concentration is 20 mg/g, is 450 Pa or higher, such as 600 Pa or higher or 700 Pa or higher, or even 800 Pa or higher. In a preferred embodiment, the elastic modulus G' of the product, when the HA concentration is 20 mg/g, is 1200 Pa or lower, such as 1100 Pa or lower, or even 1000 Pa or lower. A suitable range for the elastic modulus G' of the product is 800-1200 Pa when the HA concentration is 20 mg/g. It is preferred that the elastic modulus G' is within the limits set out above also for the corresponding cross-linked HA gel product following autoclaving by heat.

The gel content of the resulting cross-linked HA product describes in % the proportion of the total HA that is bound in gel form, i.e. the proportion that cannot be removed by filtration or dialysis. In a preferred embodiment, the gel content of the product is 80% or higher, such as 90% or higher. It is preferred that the gel content is within the limits set out above also for the corresponding cross-linked HA gel product following autoclaving by heat.

The product according to the invention can be manufactured in various shapes, such as a particle, a fibre, a string, a strand, a net, a film, a disc or a bead. It is preferred that the shape has an extension of less than 5 mm, preferably less than 1 mm, and larger than 0.5 mm or even larger than 0.8 mm when the HA substrate is in swollen form in physiological saline. A preferred shape is particles or beads having a size of 0.1-5 mm, such as 0.5-1 mm, when fully swollen in physiological saline.

The desired shape and size can be achieved by subjecting the gel to mechanical disruption, such as mincing, mashing or passing the swollen or partly swollen gel through a filter or mesh with suitable pore size. The resulting gel particles or pieces are dispersed in a physiological salt solution, resulting in a gel dispersion or slurry with particles of desired size and shape. Depending on the shape, the size of a gel structure may be determined in any suitable way, such as by laser diffraction, microscopy, filtration, etc, and is decided by the longest distance between two ends of the particle. For spherical structures, the diameter equals the size for this purpose.

According to one embodiment of the invention, a cross-linked HA gel product may be useful as a drug delivery device and be used in a method of drug delivery.

The cross-linked HA product according to the invention is useful for hydrating and/or vitalizing the skin. For this purpose, the product may e.g. be injected into the skin or included in a cream which is applied to the skin.

The cross-linked HA product according to the invention is useful in cosmetic or medical surgery. Non-limiting examples of cosmetic surgery are dermal filling, body contouring and facial contouring, in particular facial contouring. Non-limiting examples of medical surgery are dermal filling, body contouring, prevention of tissue adhesion, orthopaedic applications, incontinence treatment, treatment of vesicoureteral reflux (VUR), and formation of channels for draining purposes, e.g. in ophthalmology, and for keeping tissues apart.

According to one aspect, the present invention provides a method of treatment of a subject undergoing cosmetic or medical surgery, involving administration of a cross-linked HA product according to the invention to a subject in need thereof. Non-limiting examples of medical surgery are dermal filling, body contouring, prevention of tissue adhesion, orthopaedic applications, e.g. hip and joint therapy, and formation of channels for draining purposes, e.g. in ophthalmology, and for keeping tissues apart.

Useful gel structure size ranges and shapes depend on the intended application. For soft tissue augmentation, preferably subcutaneous administration, submuscular administration or supraperiostal administration, gel particles, pieces or fibres having a size, when subjected to a physiological salt solution, of more than 0.1 mm are useful. The term "soft tissue augmentation", as used herein, refers to any type of volume augmentation of soft tissues, including, but not limited to, facial contouring (e.g. more pronounced cheeks or chin), correction of concave deformities (e.g. post-traumatic, HIV associated lipoatrophy) and correction of deep age-related facial folds. Thus, soft tissue augmentation may be used solely for cosmetic purposes or for medical purposes, such as following trauma or degenerative disease. These two purposes are easily distinguished by the skilled person. The term "soft tissue", as used herein, refers to tissues that connect, support, or surround other structures and organs of the body. Soft tissue includes muscles, fibrous tissues and fat. Soft tissue augmentation may be performed in any mammal, including man. It is preferred that that the method is performed in a human subject.

The terms "subepidermal administration" or "subcuticular administration", as used herein, refer to administration beneath the epidermis of the skin, including administration into the dermis, subcutis or deeper, such as submuscularly or into the periosteum where applicable (in the vicinity of bone tissue).

Administration of gel structures may be performed in any suitable way, such as via injection from standard cannulae and needles of appropriate sizes or surgical insertion, e.g. in the case of administration of a film. The administration is performed where the soft tissue augmentation is desired, such as the chin, cheeks or elsewhere in the face or body. It is preferred to utilize the gel and the gel structures in facial contouring.

An implant according to the invention may be an aqueous composition comprising the cross-linked HA product according to the invention, e.g. in the shape of ≥0.1 mm large HA gel structures, such as particles, beads, fibres or cut-out stripes, and optionally a buffering agent and/or a tonicity agent. The composition may typically contain a physiological salt buffer.

The composition may further comprise other suitable active substances and medical compounds, such as local anaesthetics (e.g. lidocaine hydro-chloride), anti-inflammatory drugs, antibiotics and other suitable supportive medications, e.g. bone growth factors or cells.

The cross-linked HA product according to the invention, or an aqueous composition thereof, may be provided in a pre-filled syringe, i.e. a syringe that is pre-filled with a sterilized, cross-linked HA product or an sterilized aqueous composition comprising the shaped product. Optionally, the cross-linked HA product may be kept in precipitated form in a syringe, bag or other suitable container and be brought to its non-precipitated form prior to injection or in the body following injection thereof.

It is preferred that the swelled or partly swelled, cross-linked HA product is autoclavable, since this is the most convenient way of sterilizing the final product. This allows for preparation of a sterile, cross-linked HA product.

It goes without saying that the size of the gel structures, e.g. fibres, according to the invention is dependent upon how much the gel has been allowed to swell, and the ionic strength of the buffer, solution or carrier that is included in and/or surrounding the gel structures. Throughout this specification, given structure sizes assume physiological conditions, particularly isotonic conditions. It shall be noted that, while it is preferred that the gel structures contain and are dispersed in a physiological salt solution, it is contemplated that the gel structures according to the invention can temporarily be brought to different sizes by subjecting the gel structures to a solution of another tonicity, different pH or if the gel structures have not been allowed to swell to their maximum size.

As used herein, a physiological, or isotonic, solution is a solution having an osmolarity in the range of 200-400 mOsm/l, preferably 250-350 mOsm/l, more preferably approximately 300 mOsm/l.

The cross-linked HA gel product according to the invention is stable, but not permanent, under physiological conditions. According to an embodiment of the invention, at least 70%, preferably at least 90%, of the cross-linked HA gel product remains for at least two weeks in vivo, more preferably between two weeks and two years. The term "degraded" implies that less than 20%, preferably less than 10%, of the medium remains in the body.

Experimental Section
Analytical Methods
Determination of HA Concentration

The method for determination of HA content is adopted from the assay test for sodium hyaluronate described in Ph. Eur. 1472. The principle for the method is that a condensation reaction of the furfural derivatives formed by heating in sulphuric acid occurs with the carbazole reagent, forming a purpur colored product. The reaction is specific for the D-glucuronic acid part of HA. The absorbance is measured at 530 nm and glucuronic acid is used for standardization.

The product formed from the content of D-glucuronic acid (GlcA) in the sample is determined by reaction with carbazole. To get homogeneous sample solutions, the stabilized gel of HA is degraded with sulphuric acid at 70° C. and diluted with 0.9% NaCl-solution. The solutions are mixed with sulphuric acid at 95° C. and thereafter with carbazole reagent. The reactions result in pink coloured solutions. The intensity of the colour is measured with a colorimeter at 530 nm, and the absorbance of each sample is directly proportional to the GlcA-content. The HA content is calculated from the GlcA-content in each sample.

Determination of Gel Content (GelC)

GelC describes in % the proportion of the total HA that is bound in gel form. Gel content is defined as the amount of HA in a sample that does not pass through a 0.22 µm filter. GelC is calculated from the amount of HA that is collected in the filtrate, here denoted extractable HA. The gel content and the extractable HA content are given in percent of the total amount of HA in the gel sample. In short, the gel content is determined by mixing a certain amount of gel sample with 0.9% NaCl in a test tube. The gel is allowed to swell where after the NaCl-phase is separated from the gel-phase by filtration through a 0.22 µm filter. The concentration of HA in the filtrate is determined according to the procedure for determination of HA concentration.

Determination of Degree of Modification (MoD)

MoD describes the molar amount of bound cross-linking agent(s) relative to the total number of repeating HA disaccharide units (Kenne et al., Carbohydrate Polymers 91 (2013) 410-418). This measure does not distinguish between mono-linked and actually cross-linked cross-linking agent(s), i.e. all cross-linking agent(s) that is bound to HA via at least one covalent bond is included. For instance, a MoD of 1% for a HA gel cross-linked with BDDE means that there is 1 bound (mono-linked or cross-linked) molecule of BDDE per 100 disaccharide units in the HA gel.

MoD is determined using NMR spectroscopy on enzymatically degraded gel product. Soluble HA, residual (non-bound) cross-linking agent(s) and derivatives thereof are washed away prior to the degradation of the gel by filtration on a 0.22 µm filter. The gel product is degraded at 37° C. by enzymatic treatment using chondroitinase. The degraded gel product is subjected to NMR spectroscopy by recording one-dimensional $^1$H NMR spectra on a 500 MHz spectrometer, equipped with a standard 5 mm probe.

The NMR spectra are evaluated by integration of the signal(s) originating from protons in bound cross-linking agent, and the signals at δH 2.0 ppm, which is from the three protons in the CH$_3$ groups on the N-acetyl-glucosamine residues of the HA disaccharides. The ratio between the integrals for these two signals is proportional to the ratio between the molar amount of bound cross-linking agent and disaccharides after correction for the number of protons responsible for each signal, hence giving MoD.

$$MoD = \frac{n_{bound\ crosslinking\ agent}}{n_{disaccharide\ units}}$$

Binding Efficiency (BE)

BE describes in % the molar amount of bound cross-linking agent(s) relative to the molar amount of cross-linking agent(s) added to the cross-linking reaction. This measure does not distinguish between mono-linked and actually cross-linked cross-linking agent(s), i.e. all cross-linking agent(s) that is bound to HA via at least one covalent bond is included.

Rheometry

Rhemometry in the oscillating mode is used to determine the viscoelastic properties of the swelled gel product. The elastic modulus (G') describes the gel strength in terms of the gels physical resistance to elastic deformation. The viscous modulus (G") describes the gel strength in terms of the gel's physical resistance to viscous deformation. The measurement is performed using an oscillating rheometer.

Rheometry measurements are performed as follows. Frequency sweeps are made with a resting time of at least 15 minutes between sample loading and measurement, and a strain (γ) of 0.1%. A parallel plate probe with a diameter of 25 mm is used with a gap of 1 or 2 mm. Average values of the elastic modulus (G') and viscous modulus (G") are evaluated at 0.1 and 1 Hz from the frequency sweeps. Amplitude sweeps are made at 1 Hz to verify that the frequency sweep was performed at a strain (γ) within the linear viscoelastic range.

For rheology measurements, such as G', it is important to have a fixed gel concentration is important for comparison between different samples. A suitable fixed gel concentration used herein is an HA concentration of 20 mg/g.

EXAMPLES

Example 1

HA was transferred to a plastic jar. Solutions of NaOH at various concentrations (0.6-8.0% (w/w)) and BDDE were mixed in a shaker with high initial concentrations of HA (11, 25 or 33% (w/w) of the final mixture). The jar was transferred to an incubator or a water bath to perform the cross-linking step.

The resulting gel was allowed to swell to a HA concentration of about 20 mg/g in a buffer solution containing sodium phosphate, HCl and NaCl, at a pH about 7.5. The pH of the swollen gel was adjusted to about 7.2. The gel was filled in syringes and then autoclaved.

Example 2

The autoclaved gels manufactured in Example 1 were analyzed to determine the binding efficiency (BE), degree of modification (MoD), gel content (GelC) and elastic modulus G'. The results are presented in FIG. 1-4.

Example 2a

The binding efficiency for the added cross-linking agent is presented as a function of hydroxide concentration for the tested initial HA concentrations in FIG. 1. It is observed that the binding efficiency increases with hydroxide concentration at lower hydroxide concentrations. The binding efficiency has a peak in the range of 1.5-4% (w/w) hydroxide, with a shift towards higher hydroxide concentrations for higher initial HA concentrations. Thereafter, the binding efficiency decreases with hydroxide concentration at higher hydroxide concentrations. This shows that when cross-linking with BDDE at the higher initial HA concentrations employed herein, the hydroxide concentration range should be carefully adjusted to provide efficient incorporation into the HA, especially at initial HA concentrations of 20% or higher.

Example 2b

Figure 2:
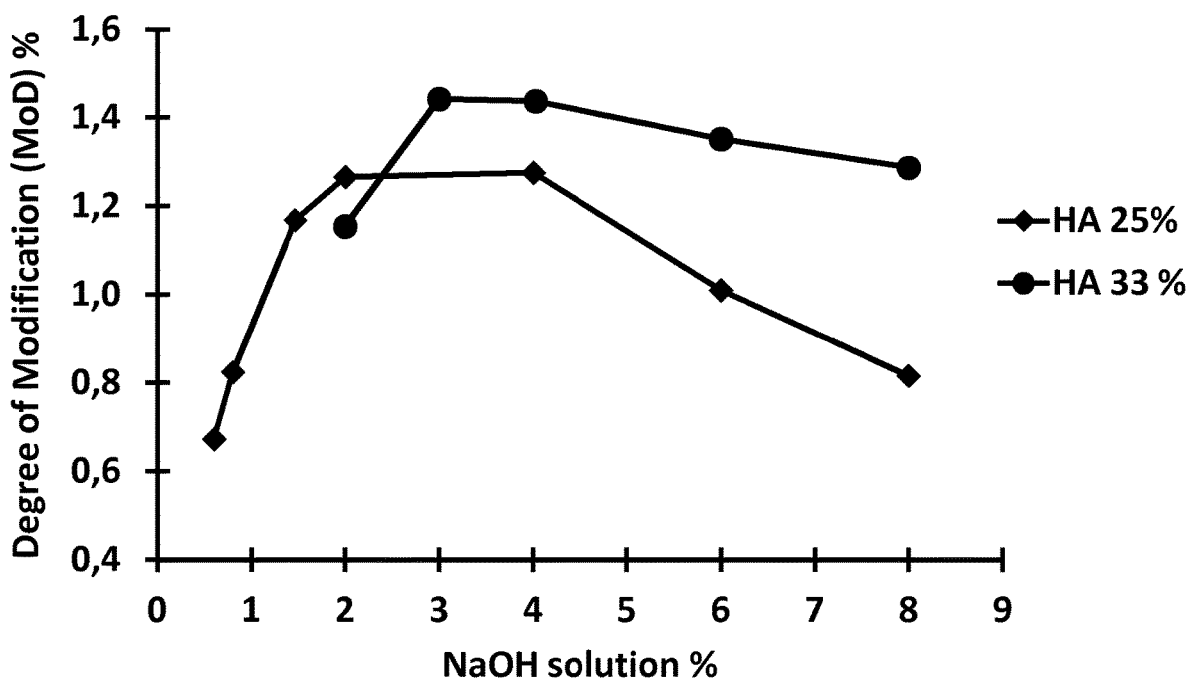
FIG. 2 shows a graph of the degree of modified HA in the cross-linked HA gel product as a function of hydroxide concentration for certain HA concentrations.

The degree of modified HA in the cross-linked HA gel product is presented as a function of hydroxide concentration for certain initial HA concentrations in FIG. 2. It is observed that the degree of modification (MoD) increases with hydroxide concentration at lower hydroxide concentrations. The MoD has a peak in the range of 2-4% (w/w) hydroxide, with a shift towards higher hydroxide concentrations for higher initial HA concentrations. Thereafter, the MoD decreases with hydroxide concentration at higher hydroxide concentrations. This shows that when cross-linking with BDDE at the higher initial HA concentrations employed herein, the hydroxide concentration range should be carefully adjusted to achieve sufficient modification of HA and provide a denser cross-linked network of HA chains.

Example 2c

Figure 3:
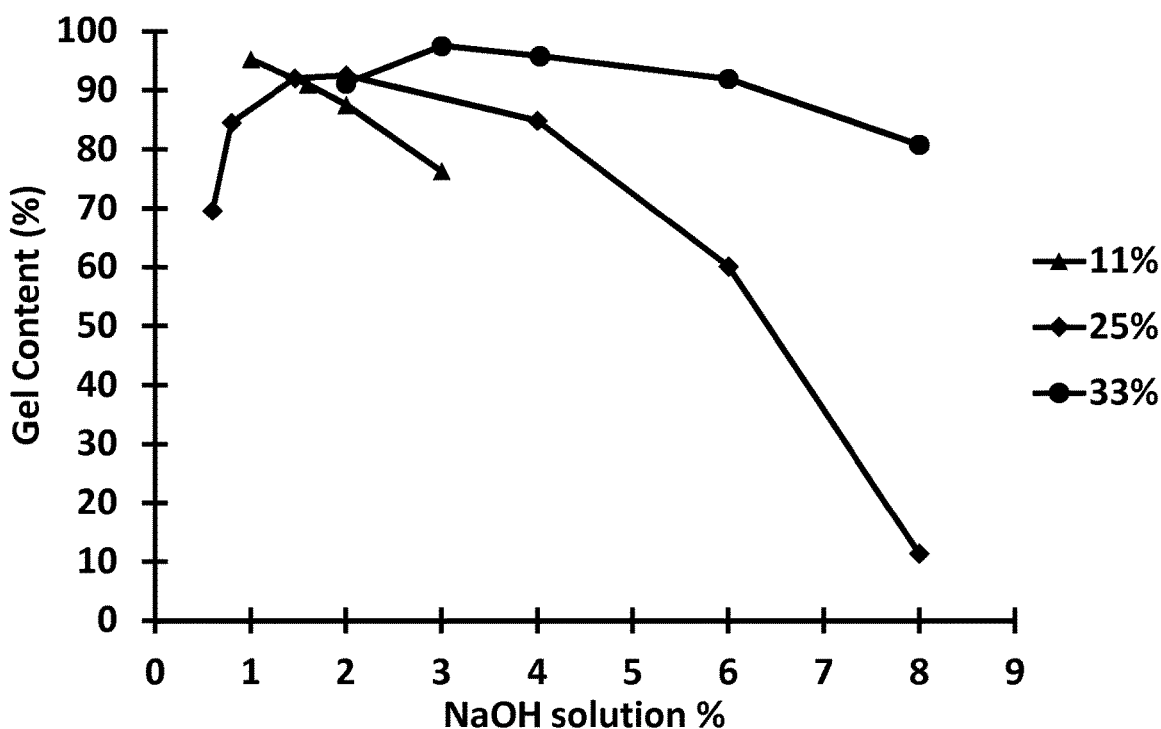
FIG. 3 shows a graph of the gel content in the cross-linked HA product as a function of hydroxide concentration for certain HA concentrations.

The gel content in the cross-linked HA product is presented as a function of hydroxide concentration for certain initial HA concentrations in FIG. 3. It is observed that the gel content increases with hydroxide concentration at lower hydroxide concentrations. The gel content has a peak in the range of 1.5-4% (w/w) hydroxide, with a shift towards higher hydroxide concentrations for higher initial HA concentrations. Thereafter, the gel content decreases with hydroxide concentration at higher hydroxide concentrations. This shows that when cross-linking with BDDE at the higher initial HA concentrations employed herein, the hydroxide concentration range should be carefully adjusted to increase the gel content of the cross-linked HA product.

Example 2d

Figure 4:
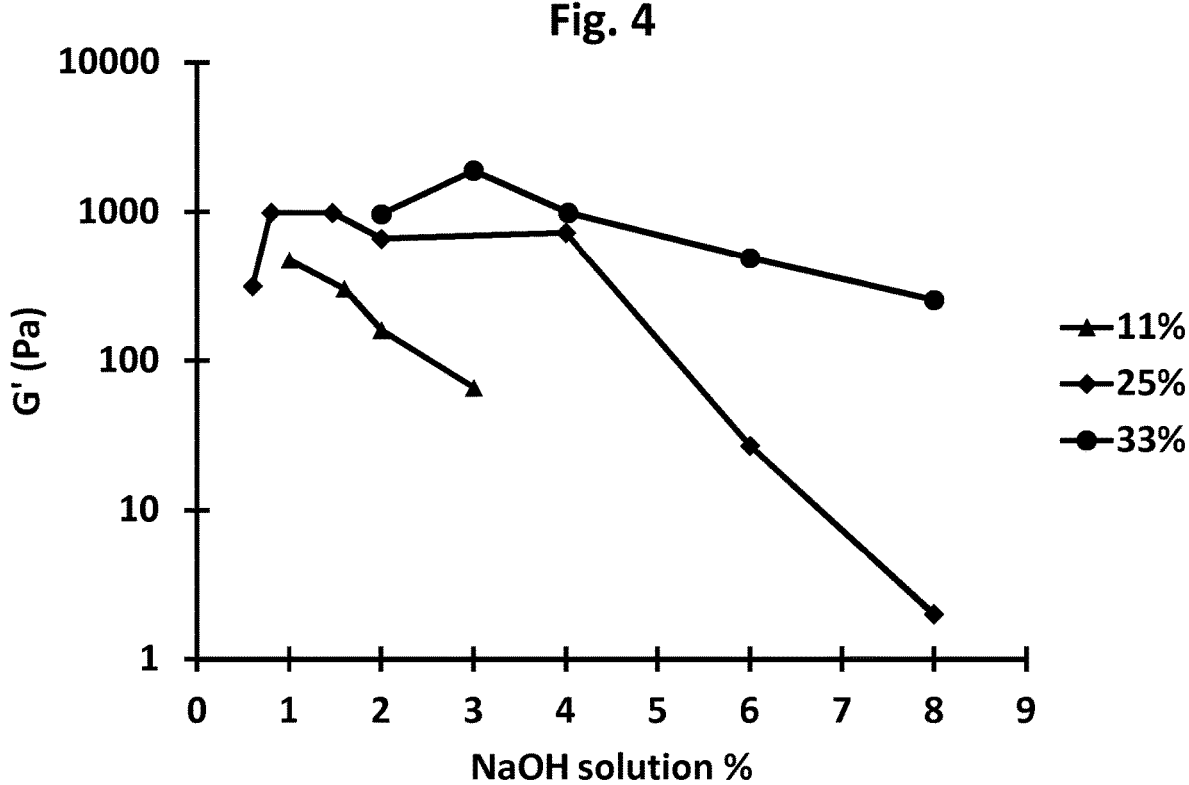
FIG. 4 shows a graph of the elastic modulus G' of the cross-linked HA gel product as a function of hydroxide concentration for certain HA concentrations.

The elastic modulus G' of the cross-linked HA gel product is presented as a function of hydroxide concentration for certain initial HA concentrations in FIG. 4. It is observed that the G' increases with hydroxide concentration at lower hydroxide concentrations. The G' has a peak in the range of 1.5-4% (w/w) hydroxide, with a shift towards higher hydroxide concentrations for higher initial HA concentrations. Thereafter, the G' decreases with hydroxide concentration at higher hydroxide concentrations. This shows that when cross-linking with BDDE at the higher initial HA concentrations employed herein, the hydroxide concentration range should be carefully adjusted to increase G' and provide a firmer gel product.

Example 3

HA was transferred to plastic jars. A 3% (w/w) NaOH solution was mixed with BDDE in a shaker with an HA concentration of 33% (w/w) of the final mixture. The jars were transferred to an incubator or a water bath to perform the cross-linking step at room temperature (RT) for 16 h, 24 h and 40 h, respectively, or for 16 h at 29° C.

The resulting gels were allowed to swell to 20 mg/g HA in a buffer solution containing sodium phosphate, HCl and NaCl, at a pH about 7.5. The gels were filled in syringes and then autoclaved.

Results:

| Cross-linking conditions | GelC (%) | G' (Pa) |
|---|---|---|
| RT -16 h | 96 | 1537 |
| 29° C. -16 h | 97 | 1384 |
| RT -24 h | 96 | 1838 |
| RT -40 h | 95 | 1845 |

The cross-linking reaction yields a gel with useful properties, e.g. gel strength, both at RT and 29° C. for reaction times of 16-40 h.

Example 4

HA was transferred to plastic jars. Solutions of 3 and 4% (w/w) NaOH, respectively, were mixed with BDDE in a shaker with an HA concentration of 33% (w/w) of the final mixture. The jars were transferred to a water bath to perform the cross-linking step for 4.5 h and 16 h, respectively, at 35° C.

The resulting gels were allowed to swell to 20 mg/g HA in a buffer solution containing sodium phosphate, HCl and NaCl, at a pH about 7.5. The gels were filled in syringes and then autoclaved.

Results:

| Cross-linking conditions | GelC (%) | G' (Pa) |
|---|---|---|
| 35° C. - 4.5 h | 94 | 767 |
| 35° C. - 16 h | 90 | 899 |

The cross-linking reaction yields a gel with useful properties, e.g. gel strength, at 35° C. for reaction times of 4.5-16 h.

Example 5

HA was transferred to plastic jars. A 2.5% (w/w) NaOH solution was mixed with BDDE in a shaker with an HA concentration of 18% (w/w) of the final mixture. The jars were transferred to an incubator or a water bath to perform the cross-linking step for 24 h, 48 h or 72 h, respectively, at RT.

The resulting gels were allowed to swell to 20 mg/g HA in a buffer solution containing sodium phosphate, HCl and NaCl, at a pH about 7.5. The gels were filled in syringes and then autoclaved.

Results:

| Cross-linking time (h) | G' (Pa) |
|---|---|
| 24 | 75 |
| 48 | 19 |
| 72 | 1 |

The cross-linking reaction yields a gel with particularly useful properties, e.g. gel strength, for reaction times of less than 48 h, such as 24 h.

Example 6

HA was transferred to plastic jar. A 1.5% (w/w) NaOH-solution was mixed with BDDE in a shaker with an HA concentration of 11% (w/w) of the final mixture. The jar was transferred to an incubator to perform the cross-linking step for 24 h at RT.

The resulting gel was allowed to swell to 20 mg/g HA in a buffer solution containing sodium phosphate, HCl and NaCl, at a pH about 7.5. The gel was filled in syringes and then autoclaved.

An aliquot of the gel was precipitated and washed in EtOH and then dried in a vacuum chamber. The gelpowder was rehydrated in a buffer solution to 20 mg/g HA. The amount of free BDDE derivatives in the solution (i.e. not coupled to the gel) was determined using LC-MS prior to and after the precipitation step.

Results:

| Gel precipitated and washed | Free derivatives (nmol/ml) |
|---|---|
| No | 3764 |
| Yes | Not detected |

This shows that an additional precipitation and washing in ethanol is highly effective to reduce undesirable soluble BDDE derivatives which are not covalently coupled to the gel product.

Example 7

HA was transferred to plastic jars. Solutions of NaOH at various concentrations (0.7-3.0% w/w) and BDDE were mixed in a shaker with HA concentrations of 18% (w/w) of the final mixture. The jars were transferred to an incubator or a water bath to perform the cross-linking step for 24 h at RT.

The resulting gels were allowed to swell to 20 mg/g HA in a buffer solution containing sodium phosphate, HCl and NaCl, at a pH about 7.5. The gels were filled in syringes and then autoclaved.

Results:

| NaOH (% w/w) | MoD (%) |
|---|---|
| 0.7 | 1.21 |
| 1.0 | 1.5 |
| 2.2 | 1.71 |
| 3.0 | 1.69 |

Example 8

BDDE Variations

HA was transferred to plastic jars. Solutions of NaOH and various BDDE concentrations were mixed in a shaker with HA concentrations of 18% (w/w) of the final mixture. The jars were transferred to an incubator or a water bath to perform the cross-linking step for 24 h at RT.

The resulting gels were allowed to swell to 20 mg/g HA in a buffer solution containing sodium phosphate, HCl and NaCl, at a pH about 7.5. The gels were filled in syringes and then autoclaved.

Results:

| BDDE (rel. conc) | MoD (%) | G' (Pa) |
| --- | --- | --- |
| 1 | 1.05 | 39 |
| 1.5 | 1.70 | 278 |
| 2.0 | 2.02 | 624 |
| 3.0 | 3.02 | 1142 |

A higher concentration of BDDE in the cross-linking reaction yields a stronger gel.

The invention claimed is:

1. A process for manufacturing a cross-linked hyaluronic acid (HA) gel product, the process comprising:
   (a) obtaining an aqueous mixture of HA and a diepoxide cross-linking agent selected from the group consisting of 1,4-butanediol diglycidyl ether (BDDE), 1,2-ethanediol diglycidyl ether (EDDE) and diepoxyoctane, wherein the HA is dissolved in an aqueous solution comprising 6-8% (w/w) inorganic hydroxide, and wherein the dissolved HA constitutes 33-35% (w/w) of the aqueous mixture; and
   (b) cross-linking the aqueous mixture at 10-75° C. to obtain the cross-linked HA gel product, wherein the HA is cross-linked in a single step.

2. The process according to claim 1, wherein the aqueous solution of (a) comprises 6% (w/w) inorganic hydroxide.

3. The process according to claim 1, wherein the aqueous solution of (a) comprises 8% (w/w) inorganic hydroxide.

4. The process according to claim 1, wherein the aqueous mixture of (a) comprises 33% (w/w) HA.

5. The process according to claim 1, wherein the aqueous mixture of (a) comprises 35% (w/w) HA.

6. The process according to claim 1, wherein the cross-linking occurs at room temperature.

7. The process according to claim 1, wherein the cross-linking is performed for 4-36 h.

8. The process according to claim 1, wherein the cross-linking agent is 1,4-butanediol diglycidyl ether (BDDE).

9. The process according to claim 1, further comprising (c) isolating the cross-linked HA product.

10. The process according to claim 9, wherein the isolating comprises precipitating the HA gel product.

11. The process according to claim 1, wherein the cross-linking is performed at 15-35° C. for 2-40 h so as to obtain the cross-linked HA gel product.

12. The process according to claim 1, wherein the cross-linking is performed at 15-35° C.

13. The process according to claim 1, wherein the cross-linked HA gel product exhibits an elastic modulus of at least 450 Pa.

* * * * *

UNITED STATES PATENT AND TRADEMARK OFFICE
CERTIFICATE OF CORRECTION

| | |
|---|---|
| PATENT NO. | : 11,021,580 B2 |
| APPLICATION NO. | : 15/747648 |
| DATED | : June 1, 2021 |
| INVENTOR(S) | : Morgan Karlsson et al. |

It is certified that error appears in the above-identified patent and that said Letters Patent is hereby corrected as shown below:

On the Title Page

Item (12) "Karlsson" should read --Karlsson et al.--

In the Inventor section, amend Inventor information as follows:
(72) Inventors: Morgan KARLSSON, Almunge, SE
        Åke ÖHRLUND, Uppsala, SE Signed and Sealed this
Thirteenth Day of August, 2024

*Katherine Kelly Vidal*
Katherine Kelly Vidal
*Director of the United States Patent and Trademark Office*